United States Patent
Prashad et al.

(10) Patent No.: US 6,933,410 B2
(45) Date of Patent: Aug. 23, 2005

(54) PROCESS FOR PREPARING 5,6-DIETHYL-2, 3-DIHYDRO-1H-INDEN-2-AMINE

(75) Inventors: Mahavir Prashad, Montville, NJ (US); Bin Hu, North Plainfield, NJ (US); Olivier Lohse, Belfort (FR)

(73) Assignee: Novartis AG, Basel (CH)

( * ) Notice: Subject to any disclaimer, the term of this patent is extended or adjusted under 35 U.S.C. 154(b) by 330 days.

(21) Appl. No.: 10/367,402

(22) Filed: Feb. 14, 2003

(65) Prior Publication Data

US 2003/0187301 A1 Oct. 2, 2003

Related U.S. Application Data

(60) Provisional application No. 60/362,735, filed on Mar. 8, 2002.

(51) Int. Cl.$^7$ ............................................. C07C 209/44
(52) U.S. Cl. ...................................... 564/414; 564/428
(58) Field of Search ................................. 564/414, 428

(56) References Cited

U.S. PATENT DOCUMENTS 4,820,705 A   4/1989 Nickl et al. ................. 514/247

FOREIGN PATENT DOCUMENTS

| EP | 0 253 321 | 1/1988 |
|---|---|---|
| EP | 1 018 514 | 7/2000 |
| WO | 00/75114 | 12/2000 |

*Primary Examiner*—Shailendra Kumar
(74) *Attorney, Agent, or Firm*—Gregory C. Houghton; John D. Thallemer; Paivi J. Kukkola

(57) ABSTRACT

A process for preparing 5,6-diethyl-2,3-dihydro-1H-inden-2-amine and acid addition salts thereof from 2-aminoindan. The process comprises protecting the amino group of 2-aminoindan, acetylating the ring in the protected compound, reducing the acetyl group to ethyl to form a monoethyl derivative, acetylating the monoethyl derivative, reducing the acetyl group to form a diethyl derivative, deprotecting the latter by hydrolysis and recovering the product in free or salt form. The process does not use deleterious Grignard reagents or nitrites such as isoamyl nitrite, and provides high regioselectivity and high yield of 5,6-diethyl-2,3-dihydro-1H-inden-2-amine. In addition, the process uses acetyl halide as both a reactant and a solvent.

19 Claims, No Drawings

PROCESS FOR PREPARING 5,6-DIETHYL-2,3-DIHYDRO-1H-INDEN-2-AMINE

This application claims benefit of U.S. Provisional Application No. 60/362,735, filed Mar. 8, 2002, which is herein incorporated by reference.

5,6-diethyl-2,3-dihydro-1H-inden-2-amine hydrochloride has Formula (VIII)

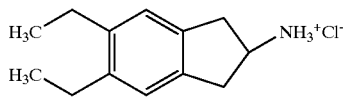

(VIII)

and has been used as an important intermediate in the synthesis of β2-adrenoceptor agonist for such indications as asthma and chronic obstructive pulmonary disorder (COPD). Previous processes for preparing 5,6-diethyl-2,3-dihydro-1H-inden-2-amine hydrochloride involve the use of Grignard reagents, poor regioselectivity during Friedel-Craft cyclization, use of isoamyl nitrite and poor yield.

EP 1018514 A1 describes indane derivatives for use as an inhibitor of NF-KB. The indane derivatives of EP 1018514 A1 are prepared using isoamyl nitrite. WO 00/75114 describes indane derivatives for use as β2-adrenoceptor agonists.

It would be desirable to develop an environmentally cleaner and safer process for preparing 5,6-diethyl-2,3-dihydro-1H-inden-2-amine and acid addition salts thereof which does not use either Grignard reagents or nitrites such as isoamyl nitrite, and provides high regioselectivity and high yield of 5,6-diethyl-2,3-dihydro-1H-inden-2-amine salt.

The present invention provides a process for preparing 5,6-diethyl-2,3-dihydro-1H-inden-2-amine comprising:

(i) protecting the amino group of 2-aminoindane with an acyl group in the presence of an organic solvent to form a compound of Formula (I)

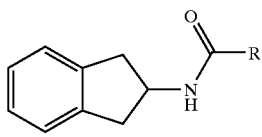

(I)

(ii) reacting the compound of Formula (I) with acetyl halide in the presence of a Lewis acid to form a compound of Formula (II)

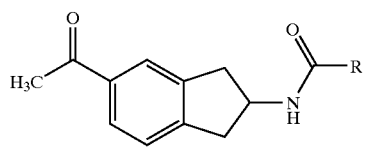

(II)

(iii) treating the compound of Formula (II) with a reducing agent in the presence of a catalyst and an organic solvent to form a compound of Formula (III)

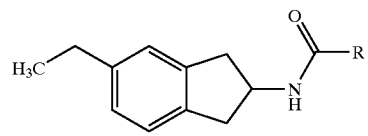

(III)

(iv) reacting the compound of Formula (III) with acetyl halide in the presence of a Lewis acid to form a compound of Formula (IV)

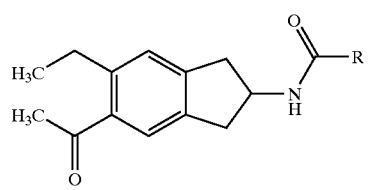

(IV)

(v) treating the compound of Formula (IV) with a reducing agent in the presence of a catalyst and an organic solvent to form a compound of Formula (V)

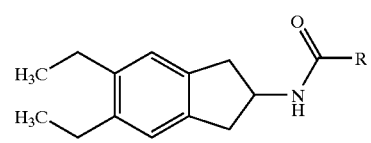

(V)

(vi) hydrolyzing the compound of Formula (V) in the presence of a base to form 5,6-diethyl-2,3-dihydro-1H-inden-2-amine of Formula (VI)

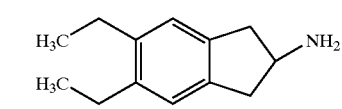

(VI)

wherein R is selected from the group consisting of an alkyl, aryl, alkoxy, alkenyl, cycloalkyl, benzocycloalkyl, cycloalkylalkyl, aralkyl, heterocyclic, heteroaralkyl and haloalkyl.

As used herein, "alkyl" means straight chain or branched alkyl, which may be, e.g., $C_1$–$C_{10}$alkyl, such as methyl, ethyl, n-propyl, isopropyl, n-butyl, isobutyl, sec-butyl, tert-butyl, straight- or branched-pentyl, straight- or branched-hexyl, straight- or branched-heptyl, straight- or branched-nonyl or straight- or branched-decyl. Preferably alkyl is $C_1$–$C_4$alkyl.

"Aryl" means $C_6$–$C_{14}$aryl, preferably $C_6$–$C_{10}$aryl, and may be, e.g., substituted by at least one group selected from mercapto, dialkylamino, nitro, alkoxy, halogen, keto, cyano or a combination. Preferably aryl is phenyl.

"Alkoxy" means straight chain or branched alkoxy and may be, e.g., $C_1$–$C_{10}$alkoxy, such as methoxy, ethoxy, n-propoxy, isopropoxy, n-butoxy, isobutoxy, sec-butoxy, tert-butoxy or straight- or branched-pentoxy, -hexyloxy, -heptyloxy, -octyloxy, -nonyloxy or -decyloxy. Preferably alkoxy is $C_1$–$C_4$alkoxy.

"Alkenyl" means straight chain or branched-alkenyl, which may be, e.g., $C_2$–$C_{10}$alkenyl, such as vinyl, 1-propenyl, 2-propenyl, 1-butenyl, isobutenyl, or straight- or branched-pentenyl, -hexenyl, -heptenyl, -octenyl, -nonenyl or -decenyl. Preferred alkenyl is $C_2$–$C_4$alkenyl.

"Cycloalkyl" means $C_3$–$C_{10}$cycloalkyl having 3- to 8-ring carbon atoms and may be, e.g., cyclopropyl, cyclobutyl, cyclopentyl, cyclohexyl, cycloheptyl or cycloheptyl, any of which can be substituted by one, two or more $C_1$–$C_4$alkyl groups, particularly methyl groups. Preferably, cycloalkyl is $C_3$–$C_6$cycloalkyl.

"Benzocycloalkyl" means cycloalkyl, e.g., one of the $C_3$–$C_{10}$cycloalkyl groups mentioned hereinbefore, attached at two adjacent carbon atoms to a benzene ring. Preferably, benzocycloalkyl is benzo-$C_5$–$C_6$cycloalkyl, especially, benzocyclohexyl (tetrahydronaphthyl).

"Cycloalkylalkyl" means $C_3$–$C_{10}$cycloalkyl$C_1$–$C_{10}$alkyl, where the $C_3$–$C_{10}$cycloalkyl group has 3- to 8-ring carbon atoms and may be, e.g., one of the $C_1$–$C_{10}$alkyl groups mentioned hereinbefore, particularly one of the $C_1$–$C_4$alkyl groups, substituted by one of the $C_3$–$C_{10}$cycloalkyl groups mentioned hereinbefore. Preferably cycloalkylalkyl is $C_3$–$C_6$cycloalkyl$C_1$–$C_4$alkyl.

"Aralkyl" means straight-chain or branched-$C_6$–$C_{10}$aryl$C_1$–$C_{10}$alkyl and may be, e.g., one of the $C_1$–$C_{10}$alkyl groups mentioned hereinbefore, particularly one of the $C_1$–$C_4$alkyl groups, substituted by phenyl, tolyl, xylyl or naphthyl. Preferably, aralkyl is phenyl$C_1$–$C_4$alkyl, particularly benzyl or 2-phenylethyl.

"Heterocyclic" means a monovalent heterocyclic group having up to 20 carbon atoms and one, two, three or four heteroatoms selected from nitrogen, oxygen and sulfur, the group optionally having an alkyl, alkylcarbonyl, hydroxyalkyl, alkoxyalkyl or aralkyl group attached to a ring carbon or nitrogen atom and being linked to the remainder of the molecule through a ring carbon atom, and may be, e.g., a group, preferably a monocyclic group, with one nitrogen, oxygen or sulfur atom, such as pyrryl, pyridyl, piperidyl, furyl, tetrahydrofuryl or thienyl, or a group, preferably a monocyclic group, with two hetero atoms selected from nitrogen, oxygen and sulfur, such as imidazolyl, pyrimidinyl, piperazinyl, oxazolyl, isoxazolyl, thiazolyl, morpholinyl or thiomorpholinyl. Preferably, heterocyclic is a monocyclic group having 5- or 6-ring atoms and one or two nitrogen atoms, or one nitrogen atom and one oxygen atom, in the ring and optionally substituted on a ring nitrogen atom by $C_1$–$C_4$alkyl, hydroxy$C_1$–$C_4$alkyl, $C_1$–$C_4$alkylcarbonyl or phenyl$C_1$–$C_4$alkyl.

"Heteroaralkyl" means straight-chain or branched-aralkyl, e.g., one of the $C_6$–$C_{10}$aryl$C_1$–$C_{10}$alkyl groups mentioned hereinbefore, substituted by one or more heterocyclic groups.

"Haloalkyl" means straight-chain or branched-alkyl, e.g., $C_1$–$C_{10}$alkyl, such as one of the $C_1$–$C_{10}$alkyl groups mentioned hereinbefore, substituted by one or more, e.g., one, two or three, halogen atoms, preferably fluorine or chlorine atoms. Preferably haloalkyl is $C_1$–$C_4$alkyl substituted by one, two or three fluorine or chlorine atoms.

Preferably in Step (i), 2-aminoindan is reacted with ethyl trifluoroacetate to form N-(2,3-dihydro-1H-inden-2-yl)-2,2,2-trifluoroacetamide.

The organic solvent in Step (i) is preferably selected from an ester of acetic acid, toluene, tetrahydrofuran, t-butyl methyl ether, and dimethylformamide. A combination of organic solvents may also be used. More preferably, the organic solvent in Step (i) is an ester of acetic acid such as methyl acetate, ethyl acetate, isopropyl acetate, and butyl acetate. Most preferably, the organic solvent in Step (i) is isopropyl acetate.

The temperature in Step (i) is preferably from about –10° C. to about 100° C. More preferably, the temperature in Step (i) is from about 0° C. to about 35° C.

The compound of Formula (I) may optionally be purified using conventional purification methods, such as by crystallization.

Preferably in Step (ii), N-(2,3-dihydro-1H-inden-2-yl)-2,2,2-trifluoroacetamide is reacted with acetyl halide in the presence of a Lewis acid to form N-(5-acetyl-2,3-dihydro-1H-inden-2-yl)-2,2,2-trifluoroacetamide having Formula (X)

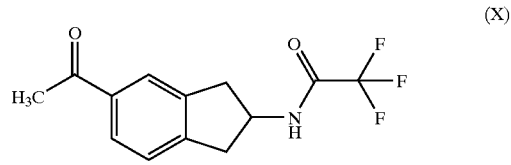

The acetyl halide is preferably selected from acetyl chloride, acetyl fluoride, acetyl bromide and acetyl iodide. A combination of acetyl halides may also be used. More preferably, the acetyl halide is acetyl chloride. It is within the scope of the invention to use acetyl halide as both a reactant and as a solvent in Step (ii).

In addition to acetyl halide, suitable solvents for use in Step (ii) include solvents used in Friedel-Crafts reactions. Preferred solvents are dichloromethane, 1,2-dichloroethane, 1,2-dichlorobenzene, and ionic liquids, such as dialkylimidazolium halides. A combination of solvents may also be used.

The Lewis acid is preferably selected from $BF_3$, $AlCl_3$, $TiCl_4$, $SnCl_4$, $BCl_3$, $(C_2H_5)_2AlCl$ and $C_2H_5AlCl_2$. A combination of Lewis acids may also be used. More preferably, the Lewis acid is aluminum chloride.

The temperature in Step (ii) is preferably from about –10° C. to about 30° C. More preferably, the temperature in Step (ii) is from about –5° C. to about 25° C.

The compound of Formula (II) may optionally be purified using conventional purification methods, such as by crystallization.

Preferably in Step (iii), N-(5-acetyl-2,3-dihydro-1H-inden-2-yl)-2,2,2-trifluoroacetamide is treated with hydrogen gas to form N-(5-ethyl-2,3-dihydro-1H-inden-2-yl)-2,2,2-trifluoroacetamide having Formula (XI)

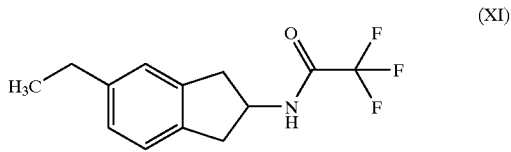

The catalyst in Step (iii) is preferably selected from palladium on carbon (Pd—C); Raney-nickel; Wilkinson's catalyst $RhCl(PPh_3)_3$; chiral dirhodiumium(II) compounds $[Rh(ligand)_2]_2$, bis(1,5-Cyclooctadiene)rhodium tetrafluoroborate and bis(norbornadiene) rhodium tetrafluoroborate $[Rh(diene)_2]BF_4$; palladium acetate $Pd(OOCCH_3)_2$; tris(dibenzylideneacetone)dipalladium(0) $Pd_2(dba)_3$; dichlorobis(triphenylphosphine)palladium(II) $PdCl_2(PPh_3)_2$; [bis(diphenylphosphino)ferrocene]palladium(II) $Cp_2Fe(PPh_2)_2PdCl_2$. A combination of catalysts may also be used. More preferably, the catalyst is palladium on carbon.

The organic solvent in Step (iii) is preferably selected from an ester of acetic acid, toluene, tetrahydrofuran, t-butyl methyl ether, dimethylformamide and an alcohol. A combination of organic solvents may also be used. More preferably, the organic solvent in Step (iii) is an ester of acetic acid, such as methyl acetate, ethyl acetate, isopropyl acetate and butyl acetate, or an alcohol, such as methanol or ethanol. Most preferably, the organic solvent in Step (iii) is isopropyl acetate or ethanol.

The temperature in Step (iii) is preferably from about 10° C. to about 60° C. More preferably, the temperature in Step (iii) is from about 20° C. to about 30° C.

The compound of Formula (III) may optionally be purified using conventional purification methods, such as by crystallization.

Preferably in Step (iv), N-(5-ethyl-2,3-dihydro-1H-inden-2-yl)-2,2,2-trifluoroacetamide is reacted with an acetyl halide to form N-(5-acetyl-6-ethyl-2,3-dihydro-1H-inden-2-yl)-2,2,2-trifluoroacetamide having Formula (XII)

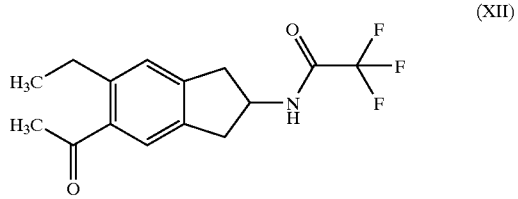

(XII)

The acetyl halide is preferably selected from acetyl chloride, acetyl fluoride, acetyl bromide and acetyl iodide. A combination of acetyl halides may also be used. More preferably, the acetyl halide is acetyl chloride. It is within the scope of the invention to use acetyl halide as both a reactant and as a solvent in Step (iv).

In addition to acetyl halide, suitable solvents for use in Step (iv) include solvents used in Friedel-Crafts reactions. Preferred solvents are dichloromethane, 1,2-dichloroethane, 1,2-dichlorobenzene, and ionic liquids, such as dialkylimidazolium halides. A combination of solvents may also be used.

The Lewis acid is preferably selected from $BF_3$, $AlCl_3$, $TiCl_4$, $SnCl_4$, $AgCl_4$, $BCl_3$, $(C_2H_5)_2AlCl$ and $C_2H_5AlCl_2$. A combination of Lewis acids may also be used. More preferably, the Lewis acid is aluminum chloride.

The temperature in Step (iv) is preferably from about −10° C. to about 30° C. More preferably, the temperature in Step (iv) is from about −5° C. to about 25° C.

The compound of Formula (IV) may optionally be purified using conventional purification methods, such as by crystallization.

Preferably in Step (v), N-(5-acetyl-6-ethyl-2,3-dihydro-1H-inden-2-yl)-2,2,2-trifluoroacetamide is treated with hydrogen gas to form N-(5,6-diethyl-2,3-dihydro-1H-inden-2-yl)-2,2,2-trifluoroacetamide having Formula (XIII)

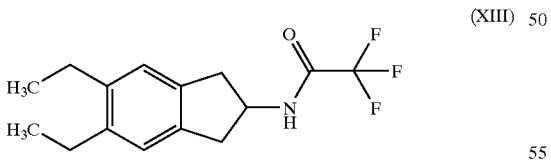

(XIII)

The organic solvent in Step (v) is preferably selected from an ester of acetic acid, toluene, tetrahydrofuran, t-butyl methyl ether, dimethylformamide and an alcohol. A combination of organic solvents may also be used. More preferably, the organic solvent in Step (v) is an ester of acetic acid, such as methyl acetate, ethyl acetate, isopropyl acetate and butyl acetate, or an alcohol, such as methanol or ethanol. Most preferably, the organic solvent in Step (v) is isopropyl acetate or ethanol.

The catalyst in Step (v) is preferably selected from palladium on carbon (Pd—C), Raney-nickel, Wilkinson's catalyst RhCl(PPh$_3$)$_3$, chiral dirhodiumium(II) compounds [Rh(ligand)$_2$]$_2$, bis(1,5-Cyclooctadiene)rhodium tetrafluoroborate and bis(norbornadiene) rhodium tetrafluoroborate [Rh(diene)$_2$]BF$_4$, palladium acetate Pd(OOCCH$_3$)$_2$, tris(dibenzylideneacetone)dipalladium(0) Pd$_2$(dba)$_3$, dichlorobis(triphenylphosphine)palladium(II) PdCl$_2$(PPh$_3$)$_2$, and [bis(diphenylphosphino)ferrocene]palladium(II) Cp$_2$Fe(PPh$_2$)$_2$PdCl$_2$. A combination of catalysts may also be used. More preferably, the catalyst is palladium on carbon.

The temperature in Step (v) is preferably from about 10° C. to about 100° C. More preferably, the temperature in Step (v) is from about 20° C. to about 60° C.

The compound of Formula (V) may optionally be purified using conventional purification methods, such as by crystallization.

Preferably in Step (vi), N-(5,6-diethyl-2,3-dihydro-1H-inden-2-yl)-2,2,2-trifluoroacetamide is hydrolyzed to form 5,6-diethyl-2,3-dihydro-1H-inden-2-amine having Formula (VI)

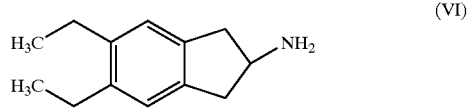

(VI)

The base is preferably selected from sodium hydroxide, lithium hydroxide and potassium hydroxide. A combination of bases may also be used. A preferred base is sodium hydroxide.

The temperature in Step (vi) is preferably from about 10° C. to about 100° C. More preferably, the temperature in Step (vi) is from about 70° C. to about 90° C.

Suitable solvents for use in Step (vi) include solvents that do not hydrolyze with the base used in Step (vi). Preferred solvents are water, tetrahydrofuran, 1,4-dioxane and an alcohol. The alcohols are preferably $C_1$–$C_6$ alcohols, such as methanol, ethanol, propanol, butanol, pentanol and hexanol. A combination of solvents may also be used.

The compound of Formula (VI) may optionally be purified using conventional purification methods, such as by crystallization.

Optionally, the compound of Formula (VI) is treated with an acid in Step (vii) to form an acid addition salt having Formula (VII)

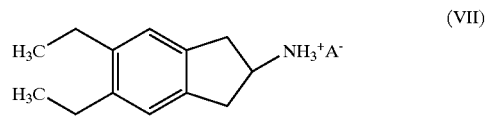

(VII)

wherein A—— is an anion. The anion corresponds to the acid used in Step (vii). A preferred anion is Cl$^-$.

Preferably in Step (vii), 5,6-diethyl-2,3-dihydro-1H-inden-2-amine is treated with hydrochloric acid to form 5,6-diethyl-2,3-dihydro-1H-inden-2-amine hydrochloride having Formula (VIII)

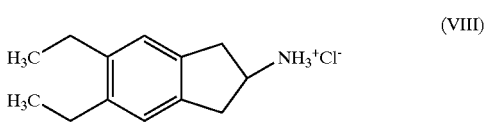

(VIII)

Essentially any acid in Step (vii) may be used to form the salt, such as mineral acids, organic carboxylic acids and organic sulfonic acids. Preferred acids include hydrochloric acid, hydrobromic acid, benzoic acid, acetic acid, citric acid, propionic acid, phosphoric acid, fumaric acid, succinic acid, sulfonic acid, methanesulfonic acid, maleic acid, bromic acid and sulfuric acid. More preferably, the acid is hydrochloric acid.

The temperature in Step (vii) is preferably from about 10° C. to about 40° C. More preferably, the temperature in Step (vii) is from about 20° C. to about 30° C.

Suitable solvents for use in Step (vii) include solvents that are soluble or miscible with the acid and 5,6-diethyl-2,3-dihydro-1H-inden-2-amine. Preferred solvents include: an ester of acetic acid, water, toluene, tetrahydrofuran, t-butyl methyl ether, dimethylformamide and an alcohol. Preferred esters of acetic acid are methyl acetate, ethyl acetate, butyl acetate and isopropyl acetate. Preferred alcohols are $C_1$–$C_6$ alcohols, such as methanol, ethanol, propanol, butanol, pentanol and hexanol. A combination of solvents may also be used.

Following preparation, the product of the process of the invention, 5,6-diethyl-2,3-dihydro-1H-inden-2-amine salt may be recovered from the reaction mixture by any of the various techniques known to the art such as filtration or centrifugation. Purification may be accomplished by crystallization.

The products of Steps (ii) to (v) are novel. Accordingly, the invention also provides compounds having the following formulas:

Formula (X)

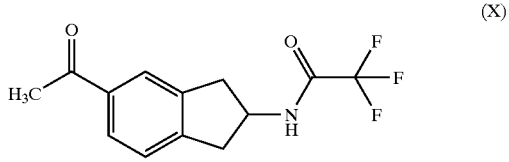

Formula (XI)

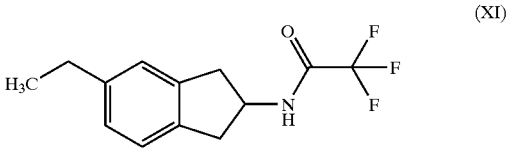

Formula (XII)

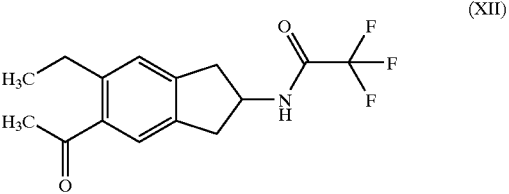

Formula (XIII)

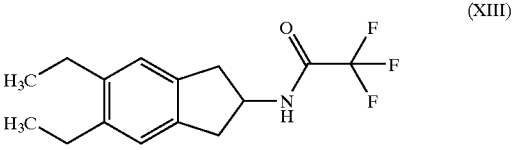

In one embodiment of the invention, the process for preparing 5,6-diethyl-2,3-dihydro-1H-inden-2-amine comprises:

(i') reacting 2-aminoindan with ethyl trifluoroacetate in an ester of acetic acid to form N-(2,3-dihydro-1H-inden-2-yl)-2,2,2-trifluoroacetamide;

(ii') reacting N-(2,3-dihydro-1H-inden-2-yl)-2,2,2-trifluoroacetamide with acetyl halide in the presence of a Lewis acid to form N-(5-acetyl-2,3-dihydro-1H-inden-2-yl)-2,2,2-trifluoroacetamide;

(iii') reducing the acetyl group of N-(5-acetyl-2,3-dihydro-1H-inden-2-yl)-2,2,2-trifluoroacetamide with hydrogen gas in the presence of a catalyst in an ester of acetic acid to form N-(5-ethyl-2,3-dihydro-1H-inden-2-yl)-2,2,2-trifluoroacetamide;

(iv') reacting N-(5-ethyl-2,3-dihydro-1H-inden-2-yl)-2,2,2-trifluoroacetamide with acetyl halide in the presence of a Lewis acid to form N-(5-acetyl-6-ethyl-2,3-dihydro-1H-inden-2-yl)-2,2,2-trifluoroacetamide;

(v') reducing the acetyl group of N-(5-acetyl-6-ethyl-2,3-dihydro-1H-inden-2-yl)-2,2,2-trifluoroacetamide with hydrogen gas in the presence of a catalyst in an ester of acetic acid to form N-(5,6-diethyl-2,3-dihydro-1H-inden-2-yl)-2,2,2-trifluoroacetamide; and (vi') hydrolyzing N-(5,6-diethyl-2,3-dihydro-1H-inden-2-yl)-2,2,2-trifluoroacetamide in the presence of a base to form 5,6-diethyl-2,3-dihydro-1H-inden-2-amine.

The following non-limiting examples illustrate further aspects of the invention.

EXAMPLE 1

Preparation of N-(2,3-dihydro-1H-inden-2-yl)-2,2,2-trifluoroacetamide, according to Step (i) of the process of the invention.

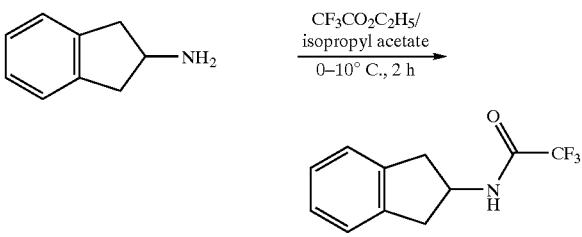

A 1 L, 3-necked, round-bottomed flask, equipped with a mechanical stirrer, digital thermometer, cooling bath, and nitrogen inlet-outlet, was charged with 2-aminoindan, (104 g, 0.781 mole) and isopropyl acetate (200 mL) at 20–25° C. The solution was cooled to 0–5° C. Ethyl trifluoroacetate (133 g, 0.936 mol) was added over 40 minutes while maintaining the internal temperature at 0–10° C. (in a 0–5° C. bath). The thick slurry was stirred at 0–10° C. for 2 hours. The reaction mixture is warmed to 20–25° C. over 30 minutes and heptane (60 mL) was added. The slurry was stirred for 30 minutes and the solids were collected by filtration over a polypropylene filter paper in a Büchner funnel with suction. The filter cake was washed with 0.003% (w/v) Stadis-450 (4.5 mg Lot # 200 Dolder)/heptane (3×50 mL) or until the filtrate was colorless. The solids were dried at 60–65° C. under vacuum (10–30 torr) with nitrogen bleeding to obtain 149.2 g (83.4% yield) of N-(2,3-dihydro-1H-inden-2-yl)-2,2,2-trifluoroacetamide as a beige white solid.

EXAMPLE 2

Preparation of N-(5-acetyl-2,3-dihydro-1H-inden-2-yl)-2,2,2-trifluoroacetamide with a halogenated solvent, dichloromethane, according to Step (ii) of the process of the invention.

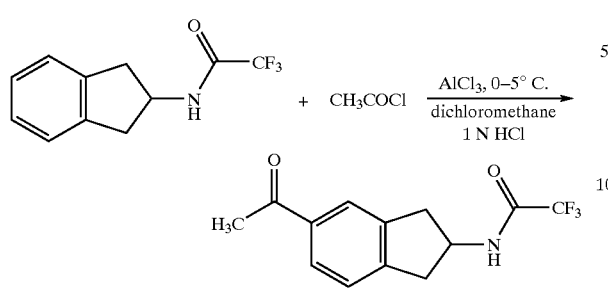

A 1 L, 4-necked, round-bottomed flask (rinsed the reactor with dichloromethane), equipped with a mechanical stirrer, digital thermometer, cooling bath, and nitrogen inlet-outlet, was charged with aluminum chloride (102 g, 0.765 mole) and 280 mL of dichloromethane at 20–25° C. The slurry was cooled to 0–5° C. Acetyl chloride (72.0 g, 0.917 mole) was added over 20 minutes, while maintaining the temperature at 0–5° C. The white suspension was stirred at 0–5° C. for 15 minutes. N-(2,3-dihydro-1H-inden-2-yl)-2,2,2-trifluoroacetamide was added in 5×14.0 g (0.305 mol, total) portions over 25 minutes at 5-minute intervals while maintaining the temperature at 0–7° C. Dichloromethane (20 mL) was added to wash off any solids sticking to the wall of the flask. The resulting tan solution was stirred at 0–5° C. for 1 hour and then added to 1 N HCl (500 mL pre-cooled to 0–5° C.) in a 2 L, 3-necked, round-bottomed flask, equipped with a mechanical stirrer, digital thermometer, and a cooling bath, while maintaining the temperature at 0–25° C. The 1 L, round-bottomed flask and a transferring tube were rinsed with dichloromethane (40 mL) and added to the batch. A bi-phasic solution was obtained. The reaction mixture was stirred and warmed to 20–25° C. The layers were separated and washed with 100 mL of water.

The organic layer was transferred to a 2 L, 4-necked, round-bottomed flask, equipped with a mechanical stirrer, digital thermometer, addition funnel, nitrogen inlet-outlet, a reflux condenser, and a heating mantle. The solution was stirred and warmed to 40±3° C. to achieve gentle refluxing. Heptane, 1200 mL, was added slowly over a period of 50 minutes while maintaining the temperature at 40–55° C. to maintain gentle refluxing. The resulting slurry was stirred at 55–58° C. for an additional 30 minutes. The suspension was cooled to 20–25° C. over a period of 30 minutes with efficient stirring. The suspension was stirred at 20–25° C. for an additional 2 hours. The solids were collected by filtration over a polypropylene filter paper in a Büchner funnel with suction and washed with a solution of dichloromethane/heptane (2×100 mL, 20:80 $^v/_v$). The solids were dried at 60–65° C. under vacuum (10–30 torr) with nitrogen bleeding to obtain 73.4 g (0.271 mole) of N-(5-acetyl-2,3-dihydro-1H-inden-2-yl)-2,2,2-trifluoroacetamide (m.p. 112–114° C., yield 88.7%).

Alternatively, the crystallization is conducted in toluene instead of heptane.

EXAMPLE 3

Preparation of N-(5-acetyl-2,3-dihydro-1H-inden-2-yl)-2,2,2-trifluoroacetamide in acetyl chloride as the solvent, according to Step (ii) of the process of the invention.

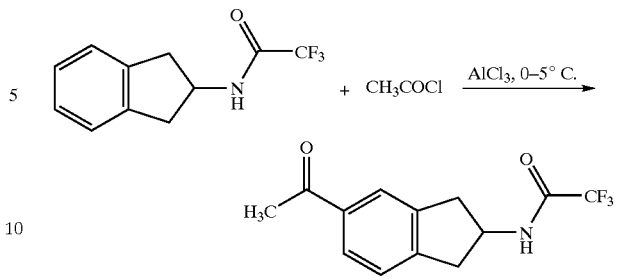

A 1 L, 3-necked, round-bottomed flask, equipped with a mechanical stirrer, digital thermometer, cooling bath, and nitrogen inlet-outlet, was charged with acetyl chloride (205.5 g, 2.62 mole) and cooled to 0–5° C. Aluminum chloride was added in portions (4×36.4 g [145.5 g, 1.09 mole]) at 0–5° C., while maintaining the internal temperature below 15° C. The slurry was cooled to 0–5° C. and stirred for 15 minutes. N-(2,3-dihydro-1H-inden-2-yl)-2,2,2-trifluoroacetamide (5×20 g, 0.436 mole) was added in portions over 40 minutes at 10-minute intervals, while maintaining temperature at 0–10° C. The resulting tan solution was stirred at 0–5° C. for 1 hour. To the solution was added 400 mL of heptane, while maintaining the temperature at 0–5° C. The resulting bi-phasic mixture was added to a 0° C. to –5° C. mixture of 1 N HCl (650 mL) and isopropyl acetate (125 mL) in a 5 L, 3-necked, round-bottomed flask, equipped with a mechanical stirrer, digital thermometer, and a cooling bath, while maintaining the internal temperature at 0–25° C. over a period of 20 minutes. The 5 L, round-bottomed flask was rinsed with acetyl chloride (20 mL), followed by heptane (110 mL) and added to the batch. The reaction mixture was warmed to 22–24° C. over a period of 30 minutes and then heated to 40–45° C. and stirred at 40–45° C. for 1 hour. The slurry was cooled to 21–25° C. and stirred for 1 hour. The solids were collected by filtration using a Büchner funnel with suction over a polypropylene filter paper. The filter cake was washed with heptane (2×200 mL) followed by 1 N HCl (350 mL), and deionized water (2×200 mL). The solids were dried at 60–65° C. under vacuum (10–30 torr) with nitrogen bleeding to obtain 106.1 g (yield 90%) of N-(5-acetyl-2,3-dihydro-1H-inden-2-yl)-2,2,2-trifluoroacetamide (m.p. 113–115° C.).

EXAMPLE 4

Preparation of N-(5-ethyl-2,3-dihydro-1H-inden-2-yl)-2,2,2-trifluoroacetamide, according to Step (iii) of the process of the invention.

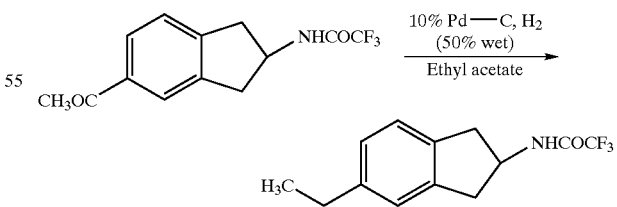

A 1 L Buchi reactor was charged with N-(5-acetyl-2,3-dihydro-1H-inden-2-yl)-2,2,2-trifluoroacetamide (100 g, 368.7 mmol), 10 g of 10% Pd—C (50% water wet), and ethyl acetate (350 mL) to obtain a suspension. The reactor was sealed and pressurized with $N_2$ to 40 psig (2,073 torr). The $N_2$ was vented and the process repeated two more times.

The reactor was again re-pressurized with N₂ to 40 psig (2,073 torr) and agitation was started at 300 rpm. The reaction mixture was heated to 25° C. and held for 10 minutes to stabilize the temperature. Agitation was stopped and the N₂ was vented. The reactor was pressurized with H₂ to 40 psig (2,073 torr), which was then vented. This process was repeated two more times and the reactor was re-pressurized with H₂ to 40 psig (2,073 torr). The in-line pressure regulator was set to maintain 40 psig (2,073 torr) of H₂ inside the reactor and the hydrogen supply valve was opened. Agitation was started at 450 rpm. The heterogeneous reaction mixture was stirred at 23–25° C. and 450 rpm for 4 hours. The hydrogen supply valve was closed and the H₂ was vented. The reactor was purged three times with N₂ and the reaction mixture was transferred to a 1 L filtration flask. The reaction mixture was filtered over a 15 g pad of Celite® (463CDH from PPO) in a Büchner funnel with suction and the filtrate was saved. The reactor vessel was rinsed with 210 mL of ethyl acetate and the filtrate filter through the Celite® pad. The cake was washed with 210 mL of ethyl acetate.

The filtrates were combined and transferred to a 2 L, 4-necked, round-bottomed flask, equipped with a mechanical stirrer, digital thermometer, addition funnel, nitrogen inlet-outlet, and heating mantle. The combined filtrates are concentrated under vacuum (150–200 mbar, 113–150 torr) at 35–40° C. to collect approximately 670 mL of solvent to obtain approximately 100 mL of a suspension. Heptane, 870 mL, was added and the solution was concentrated under vacuum (100–150 mbar, 75–113 torr) at 35–40° C. to collect approximately 270 mL of solvent to obtain approximately 700 mL of a slurry. Heptane (270 mL) was added and the suspension was concentrated under vacuum (100–150 mbar, 75–113 torr) at 35–40° C. to collect approximately 270 mL of solvent to obtain approximately 700 mL of a slurry. Heptane (270 mL) was added to obtain approximately 1000 mL of a suspension. The suspension was stirred at 35–40° C. for 30 minutes. The suspension was cooled to 20–25° C. over a period of 30 minutes with efficient stirring. Stirring was continued at this temperature for an additional 2 hours. The solids were collected by filtration over a polypropylene filter paper in a Büchner funnel with suction and washed with heptane (100 mL) containing 0.003% (w/v) Stadis-450 in two equal portions of 50 mL each. The solids were dried at 60–65° C. under vacuum (13–40 mbar, 10–30 torr) with nitrogen bleeding to obtain 87 g (91% yield) of N-(5-ethyl-2,3-dihydro-1H-inden-2-yl)-2,2,2-trifluoroacetamide (m.p. 112–114° C.).

Alternatively, the reaction solvent in Example 4 is ethanol instead of ethyl acetate, and water instead of heptane is used for the crystallization.

EXAMPLE 5

Preparation of N-(5-acetyl-6-ethyl-2,3-dihydro-1H-inden-2-yl)-2,2,2-trifluoroacetamide in acetyl chloride as the solvent, according to Step (iv) of the process of the invention.

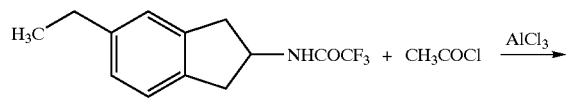

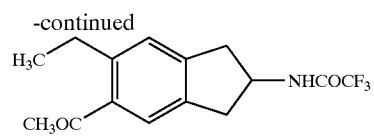

A 250 mL, 4-necked, round-bottomed flask, equipped with a mechanical stirrer, digital thermometer, cooling bath, and nitrogen inlet-outlet, was charged with acetyl chloride (37.68 g, 480 mmol) and cooled to 0±5° C. Aluminum chloride (13.33 g, 100 mmol) was added in 4×3.33 g portions at 0±5° C. while maintaining the temperature below 15° C. The resulting solution was cooled to 0±5° C. and stirred for 5 minutes. N-(5-ethyl-2,3-dihydro-1H-inden-2-yl)-2,2,2-trifluoroacetamide (10.29 g, 40 mmol) was added in 5×2.06 g portions over 40 minutes at 10-minute intervals, while maintaining the temperature 0–10° C. The tan solution was stirred at 0±5° C. for an additional 30 minutes. The solution was added to a pre-cooled (0–5° C.) mixture of 1 N HCl (120 mL) and isopropyl acetate (13 mL) in a 500 mL, 3-necked, round-bottomed flask, equipped with a mechanical stirrer, digital thermometer, and a cooling bath, while maintaining the temperature at 0–25° C. over a period of 20 minutes. The 250 mL, round-bottomed flask was rinsed with 3 mL of acetyl chloride followed by 13 mL of heptane and added to the batch. The resulting slurry was warmed to 40–45° C. over a period of 30 minutes and then stirred for additional 1 hour. Heptane (39 mL) was added and the slurry was stirred at 40–45° C. for an additional 15 minutes. The slurry was cooled to 20–25° C. and stirred for 1 hour. The solids were collected by filtration using a Büchner funnel with suction over polypropylene filter paper. The filter cake was washed with 2×10 mL heptane/isopropyl acetate (80:20 ᵛ/ᵥ), followed by 1 N HCl (36 mL) and deionized water (2×25 mL). The solids were dried at 60–65° C. under vacuum (13–40 mbar, 10–30 torr) with nitrogen bleeding to obtain 11.3 g (94% yield) of N-(5-acetyl-6-ethyl-2,3-dihydro-1H-inden-2-yl)-2,2,2-trifluoroacetamide (m.p. 124–127° C.).

EXAMPLE 6

Preparation of N-(5-acetyl-6-ethyl-2,3-dihydro-1H-inden-2-yl)-2,2,2-trifluoroacetamide with a halogenated solvent, dichloromethane, according to Step (iv) of the process of the invention.

A 2 L, 4-necked, round-bottomed flask, equipped with a mechanical stirrer, digital thermometer, addition funnel, nitrogen inlet-outlet, and heating cooling bath was charged with aluminum chloride (194.4 g, 1457.7 mmol) and dichloromethane (525 mL). The mixture was stirred to give a suspension and cooled to 0±5° C. over a period of 15 minutes. Acetyl chloride (137.3 g, 1749.2 mmol) was added over a period of 30 minutes while maintaining 0+5° C. A suspension was obtained, which was stirred at this temperature for an additional 15 minutes. N-(5-ethyl-2,3-dihydro-1H-inden-2-yl)-2,2,2-trifluoroacetamide (5×30.0 g, 583.1 mmol) was added while maintaining 0±5° C. A solution was obtained when about half of the acetamide was added. Dichloromethane (75 mL) was added to wash off any solids sticking on the wall of the flask. The solution was stirred at 0–5° C. for an additional 1 hour.

A 3 L, 4-necked, round-bottomed flask, equipped with a mechanical stirrer, digital thermometer, addition funnel, nitrogen inlet-outlet, and heating cooling bath was charged with 1 N hydrochloric acid (1000 mL) and cooled to 0–5° C.

The reaction mixture was added (maintaining 0–5° C.) to this hydrochloric acid solution over a period of 45 minutes while maintaining the temperature below 25° C. Dichloromethane (2×90 mL) was added to rinse the reaction flask and the transferring pipe and was then combined with the quenched mixture. A bi-phasic solution was obtained. The organic layer was separated and saved. The aqueous layer was extracted with dichloromethane (150 mL). The organic layer was separated. The organic layers were combined and washed with water (500 mL).

The organic layer was separated and transferred to a 2 L, 4-necked, round-bottomed flask, equipped with a mechanical stirrer, digital thermometer, addition funnel, nitrogen inlet-outlet, and heating mantle. The organic layer was concentrated under atmospheric pressure at 40±3° C. to collect approximately 700 mL of solvent to obtain approximately 340 of a solution. Heptane (1125 mL) was added over a period of 15 minutes while maintaining the temperature at 40–50° C. (gentle refluxing) with efficient stirring. A solid precipitated out. The resulting suspension was stirred at 55±3° C. (gentle refluxing) for an additional 30 minutes. The suspension was cooled to 20–25° C. over a period of 1 hour with efficient stirring. The suspension was stirred at 20–25° C. for an additional 2 hours. The solids were collected by filtration over a polypropylene filter paper in a Büchner funnel with suction and washed with 2×100 mL heptane/dichloromethane (5:1, $^v/_v$). The solids were dried at 60–65° C. under vacuum (13–40 mbar, 10–30 torr) with nitrogen bleeding to obtain 165.1 g (94% yield) of N-(5-acetyl-6-ethyl-2,3-dihydro-1H-inden-2-yl)-2,2,2-trifluoroacetamide (m.p. 124–127° C.).

Alternatively, the crystallization in Example 6 is conducted with a 1:1 ethanol/water mixture instead of heptane.

EXAMPLE 7

Preparation of N-(5,6-diethyl-2,3-dihydro-1H-inden-2-yl)-2,2,2-trifluoroacetamide according to Step (v) of the process of the invention.

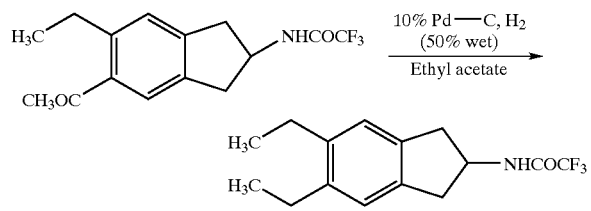

A 1 L Buchi reactor is charged with of N-(5,6-acetyl-6-ethyl-2,3-dihydro-1H-inden-2-yl)-2,2,2-trifluoroacetamide 160 g (534.6 mmol), 10% Pd—C (50% water wet) (16 g), and ethyl acetate (560 mL) to obtain a suspension. The reactor was sealed and then pressurized with $N_2$ to 40 psig (2,073 torr), which was then vented. This process was repeated two more times. The reactor was re-pressurized with $N_2$ to 40 psig (2,073 torr) and agitation was started at 650 rpm. The reaction mixture was heated to 25° C. and held for 10 minutes to stabilize the temperature. Agitation was stopped and the $N_2$ was vented. The reactor was pressurized with $H_2$ to 40 psig (2,073 torr) and then vented. This process was repeated two more times. The reactor was re-pressurized with $H_2$ to 40 psig (2,073 torr) and the in-line pressure regulator set to maintain 40 psig (2,073 torr) $H_2$. The hydrogen supply valve was opened and agitation was started at 650 rpm. The heterogeneous reaction mixture was stirred at 20–25° C. and 650 rpm for 2 hours. The reaction mixture was heated to 45–50° C. over a period of 30 minutes. The mixture was stirred at this temperature for additional 3 hours. The reaction mixture was stirred and cooled to 20–25° C. over a period of 30 minutes. The hydrogen supply valve was closed and the $H_2$ was vented. The reactor was purged three times with $N_2$. The reaction mixture was transferred to a 1 L filtration flask. The reaction mixture was filtered over a pad of 24 g of Celite® in a Büchner funnel with suction. The filtrate was saved. The reactor was rinsed with ethyl acetate (336 mL) which was filtered through the Celite® pad. The cake was washed with 336 mL of ethyl acetate. The filtrates were combined and transferred to a 5 L, 4-necked, round-bottomed flask, equipped with a mechanical stirrer, digital thermometer, addition funnel, nitrogen inlet-outlet, and heating mantle. The filtrates were concentrated under vacuum (150–200 mbar, 113–150 torr) at 35–40° C. to collect approximately 1140 mL of solvent to obtain approximately 240 mL of a suspension. Heptane (1400 mL) was added and the suspension was concentrated under vacuum (120–180 mbar, 90–135 torr) at 35–40° C. to collect approximately 680 mL of solvent to obtain approximately 960 mL of a slurry. Heptane (1,600 mL) was added to obtain approximately 2,560 mL of a suspension. The suspension was stirred at 45–50° C. for 3 hours. The suspension was cooled to 20–25° C. over a period of 1 hour with efficient stirring and stirred at this temperature for additional 2 hours. The solids were collected by filtration over a polypropylene filter paper in a Büchner funnel with suction and washed with heptane (2×250 mL) containing Stadis-450 (003% $^w/_v$). The solids were dried at 60–65° C. under vacuum (13–40 mbar, 10–30 torr) with nitrogen bleeding to obtain 133.5 g (87.5% yield) of N-(5,6-diethyl-2,3-dihydro-1H-inden-2-yl)-2,2,2-trifluoroacetamide.

Alternatively, the reaction solvent in Example 7 is ethanol instead of ethyl acetate, and water instead of heptane is used for the crystallization.

EXAMPLE 8

Preparation of 5,6-diethyl-2,3-dihydro-1H-inden-2-amine monohydrochloride according to Step (vi) and Step (vii) of the process of the invention.

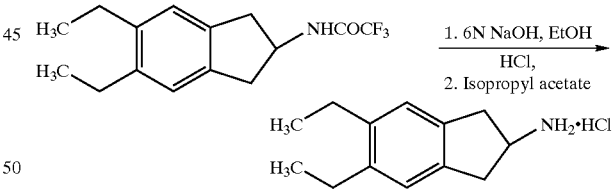

A 2 L, 4-necked, round-bottomed flask, equipped with a mechanical stirrer, digital thermometer, addition funnel, nitrogen inlet-outlet, and heating cooling bath, was charged with N-(5,6-diethyl-2,3-dihydro-1H-inden-2-yl)-2,2,2-trifluoroacetamide (100 g, 350.5 mmol), 200 proof ethanol (500 mL), and 6 N NaOH (500 mL). The mixture is stirred under nitrogen flow to give a solution and heated to 78±3° C. over a period of 30 minutes to achieve gentle refluxing. The solution is stirred at this temperature for an additional 1 hour. The solution was cooled to 30–35° C. The solution is concentrated under vacuum (60–150 mbar, 45–113 torr) at 35±5° C. to collect approximately 520 mL of solvent to obtain approximately 485 mL of a bi-phasic mixture (an oil layer floating on top of an aqueous layer). This mixture is cooled to 20–25° C. Isopropyl acetate (500 mL) was added and mixed for 5 minutes. The organic layer was separated and saved. The aqueous layer was extracted with isopropyl acetate (500 mL) and the organic layer was separated. The organic layers were combined and washed with 300 mL of water.

The organic layer was separated and concentrated under vacuum (50–150 mbar, 38–113 torr) at 35±5° C. to collect approximately 230 mL of solvent to obtain approximately 800 mL of a solution. This solution was added to 250 mL of 2 N HCl in isopropyl acetate (prepared by dissolving 18.3 g of hydrogen chloride gas in 250 mL of isopropyl acetate) over a period of 40 minutes while maintaining a temperature at 25±5° C. Solids are immediately formed. The suspension is stirred at 20–25° C. for 2 hours. The solids were collected by filtration over a polypropylene filter paper in a Büchner funnel with suction and washed with isopropyl acetate (2×100 mL). The solids were dried at 60–65° C. under vacuum (13–40 mbar, 10–30 torr) with nitrogen bleeding to obtain 78.3 g of crude 5,6-diethyl-2,3-dihydro-1H-inden-2-amine monohydrochloride.

A 2 L, 4-necked, round-bottomed flask, equipped with a mechanical stirrer, digital thermometer, addition funnel, nitrogen inlet-outlet, and a heating cooling bath, was charged with 78 g of crude 5,6-diethyl-2,3-dihydro-1H-inden-2-amine monohydrochloride and 624 mL (8 times the weight of crude solid) of 200 proof ethanol. The suspension was stirred and heated to 78±3° C. to achieve gentle refluxing. A solution was obtained. Isopropyl acetate (624 mL) was added while maintaining the temperature at 78±3° C. A precipitate is formed. The resulting suspension was stirred at this temperature for an additional 1 hour. The suspension was cooled to 20–25° C. over a period of 2 hours with efficient stirring. The suspension was stirred at 20–25° C. for an additional 2 hours. The solids were collected by filtration over a polypropylene filter paper in a Büchner funnel with suction and washed with isopropyl acetate/ethanol (70:30 $v/v$, 2×100 mL). The solids were dried at 60–65° C. under vacuum (13–40 mbar, 10–30 torr) with nitrogen bleeding to obtain 70.8 g (89% yield) of 5,6-diethyl-2,3-dihydro-1H-inden-2-amine monohydrochloride (m.p. >250° C.).

While the invention has been described with particular reference to certain embodiments thereof, it will be understood that changes and modifications may be made by those of ordinary skill within the scope and spirit of the following claims:

What is claimed is:
1. A process for preparing 5,6-diethyl-2,3-dihydro-1H-inden-2-amine comprising:

(i) protecting the amino group of 2-aminoindan with an acyl group in the presence of an organic solvent to form a compound of Formula (I)

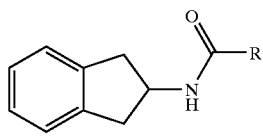

(ii) reacting the compound of Formula (I) with acetyl halide in the presence of a Lewis acid to form a compound of Formula (II)

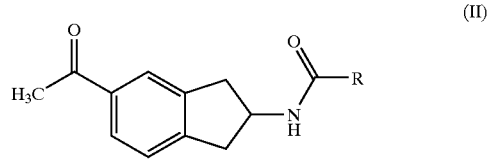

(iii) treating the compound of Formula (II) with a reducing agent in the presence of a catalyst and an organic solvent to form a compound of Formula (III)

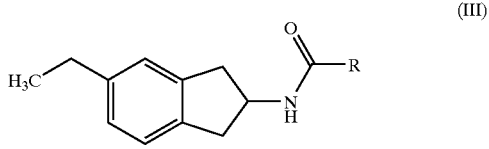

(iv) reacting the compound of Formula (III) with acetyl halide in the presence of a Lewis acid to form a compound of Formula (IV)

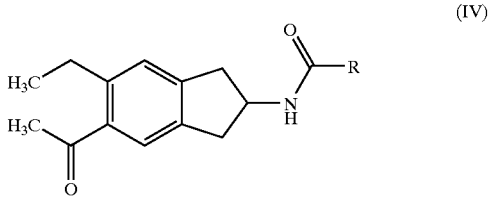

(v) treating the compound of Formula (IV) with a reducing agent in the presence of a catalyst and an organic solvent to form a compound of Formula (V)

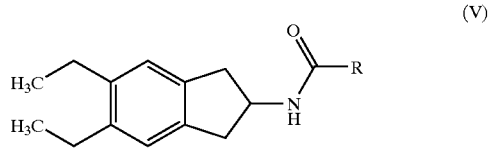

(vi) hydrolyzing the compound of Formula (V) in the presence of a base to form 5,6-diethyl-2,3-dihydro-1H-inden-2-amine of Formula (VI)

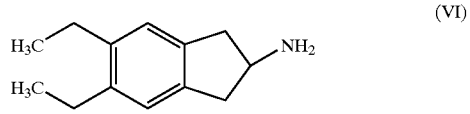

wherein R is selected from the group consisting of an alkyl, aryl, alkoxy, alkenyl, cycloalkyl, benzocycloalkyl, cycloalkylalkyl, aralkyl, heterocyclic, heteroaralkyl and haloalkyl.

2. The process according to claim 1 wherein the compound of Formula (I) is N-(2,3-dihydro-1H-inden-2-yl)-2,2,2-trifluoroacetamide; the compound of Formula (II) is N-(5-acetyl-2,3-dihydro-1H-inden-2-yl)-2,2,2-trifluoroacetamide; the compound of Formula (III) is N-(5-ethyl-2,3-dihydro-1H-inden-2-yl)-2,2,2-trifluoroecetamide; the compound of Formula (IV) is N-(5-acetyl-6-ethyl-2,3-dihydro-1H-inden-2-yl)-2,2,2-trifluoroacetamide; and the compound of Formula (V) is N-(5,6-diethyl-2,3-dihydro-1H-inden-2-yl)-2,2,2-trifluoroacetamide.

3. The process according to claim 1 which additionally comprises Step (vii) treating the compound of Formula (VI) with an acid to form a compound of Formula (VII)

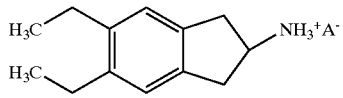
(VII)

wherein A⁻ is an anion.

4. The process according to claim 3 wherein the compound of Formula (VII) is 5,6-diethyl-2,3-dihydro-1H-inden-2-amine hydrochloride having Formula (VIII)

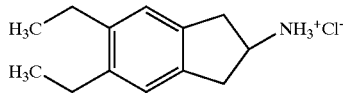
(VIII)

5. A process for preparing 5,6-diethyl-2,3-dihydro-1H-inden-2-amine comprising:
(i') reacting 2-aminoindan with ethyl trifluoroacetate in an ester of acetic acid to form N-(2,3-dihydro-1H-inden-2-yl)-2,2,2-trifluoroacetamide;
(ii') reacting N-(2,3-dihydro-1H-inden-2-yl)-2,2,2-trifluoroacetamide with acetyl halide in the presence of a Lewis acid to form N-(5-acetyl-2,3-dihydro-1H-inden-2-yl)-2,2,2-trifluoroacetamide;
(iii') reducing the acetyl group of N-(5-acetyl-2,3-dihydro-1H-inden-2-yl)-2,2,2-trifluoroacetamide with hydrogen gas in the presence of a catalyst in an ester of acetic acid to form N-(5-ethyl-2,3-dihydro-1H-inden-2-yl)-2,2,2-trifluoroacetamide;
(iv') reacting N-(5-ethyl-2,3-dihydro-1H-inden-2-yl)-2,2,2-trifluoroacetamide with acetyl halide in the presence of a Lewis acid to form N-(5-acetyl-6-ethyl-2,3-dihydro-1H-inden-2-yl)-2,2,2-trifluoroacetamide;
(v') reducing the acetyl group of N-(5-acetyl-6-ethyl-2,3-dihydro-1H-inden-2-yl)-2,2,2-trifluoroacetamide with hydrogen gas in the presence of a catalyst in an ester of acetic acid to form N-(5,6-diethyl-2,3-dihydro-1H-inden-2-yl)-2,2,2-trifluoroacetamide; and
(vi') hydrolyzing N-(5,6-diethyl-2,3-dihydro-1H-inden-2-yl)-2,2,2-trifluoroacetamide in the presence of a base to form 5,6-diethyl-2,3-dihydro-1H-inden-2-amine.

6. The process according to claim 1 wherein the acetyl halide is a reactant and a solvent in Step (ii) and/or in Step (iv).

7. The process according to claim 1 wherein the acetyl halide is independently selected from the group consisting of acetyl chloride, acetyl fluoride, acetyl bromide, acetyl iodide and combinations thereof.

8. The process according to claim 7 wherein the acetyl halide is acetyl chloride.

9. The process according to claim 1 wherein the Lewis acid is independently selected from the group consisting of $BF_3$, $AlCl_3$, $TiCl_4$, $SnCl_4$, $BCl_3$, $(C_2H_5)_2AlCl$ and $C_2H_5AlCl_2$.

10. The process according to claim 9 wherein the Lewis acid is $AlCl_3$.

11. The process according to claim 1 wherein the organic solvent is an ester of acetic acid or an alcohol.

12. The process according to claim 11 wherein the ester of acetic acid is selected from the group consisting of methyl acetate, ethyl acetate, isopropyl acetate and butyl acetate.

13. The process according to claim 11 wherein the organic solvent in Step (i) is isopropyl acetate.

14. The process according to claim 11 wherein the organic solvent in Steps (iii) and (v) is ethanol.

15. The process according to claim 1 wherein the catalyst in Steps (iii) and (v) is palladium on carbon.

16. The process according to claim 1 wherein the base is sodium hydroxide.

17. The process according to claim 1 wherein the reducing agent is hydrogen gas.

18. The process according to claim 1 wherein the temperature in Step (i) is from about −10° C. to about 100° C.; the temperature in Step (ii) is from about −10° C. to about 30° C.; the temperature in Step (iii) is from about 10° C. to about 60° C.; the temperature in Step (iv) is from about −10° C. to about 30° C.; the temperature in Step (v) is from about 10° C. to about 100° C.; and the temperature in Step (vi) is from about 10° C. to about 100° C.

19. The process according to claim 18 wherein the temperature in Step (i) is from about 0° C. to about 35° C.; the temperature in Step (ii) is from about −5° C. to about 25° C.; the temperature in Step (iii) is from about 20° C. to about 30° C.; the temperature in Step (iv) is from about −5° C. to about 25° C.; the temperature in Step (v) is from about 20° C. to about 60° C.; and the temperature in Step (vi) is from about 70° C. to about 90° C.

* * * * *